(12) United States Patent
Sato

(10) Patent No.: US 8,227,059 B2
(45) Date of Patent: Jul. 24, 2012

(54) WATER-DISINTEGRABLE SHEET AND POUCH MADE OF THE SAME FOR EXCRETA-HOLDING WEAR

(75) Inventor: Makoto Sato, Tokyo (JP)

(73) Assignee: Alcare Co., Ltd., Tokyo (JP)

( * ) Notice: Subject to any disclaimer, the term of this patent is extended or adjusted under 35 U.S.C. 154(b) by 440 days.

(21) Appl. No.: 12/514,199

(22) PCT Filed: Jul. 25, 2008

(86) PCT No.: PCT/JP2008/063364
§ 371 (c)(1),
(2), (4) Date: Jun. 8, 2009

(87) PCT Pub. No.: WO2009/014202
PCT Pub. Date: Jan. 29, 2009

(65) Prior Publication Data
US 2010/0042060 A1 Feb. 18, 2010

(30) Foreign Application Priority Data
Jul. 26, 2007 (JP) .................. 2007-194614

(51) Int. Cl.
*B29D 22/00* (2006.01)
*A61F 13/15* (2006.01)
*A61F 13/20* (2006.01)

(52) U.S. Cl. .............. 428/35.2; 604/358; 604/364

(58) Field of Classification Search .............. 428/35.2; 604/358, 364
See application file for complete search history.

(56) References Cited

U.S. PATENT DOCUMENTS

| 4,944,734 A | * | 7/1990 | Wallach | 604/358 |
| 5,158,810 A | | 10/1992 | Oishi et al. | |
| 5,478,386 A | * | 12/1995 | Itoh et al. | 428/532 |
| 7,517,339 B2 | | 4/2009 | Pedersen et al. | |
| 2005/0113770 A1 | | 5/2005 | Pedersen et al. | |

FOREIGN PATENT DOCUMENTS

| JP | 4-180753 | 6/1992 |
| JP | 6-507929 | 9/1994 |
| JP | 7-076632 | 3/1995 |
| JP | 2003-181992 | 7/2003 |
| JP | 2007-000508 | 1/2007 |
| JP | 2007-037881 | 2/2007 |
| JP | 2007-508905 | 4/2007 |
| WO | WO 92/20738 | 11/1992 |
| WO | WO 2005/041828 | 5/2005 |

\* cited by examiner

*Primary Examiner* — Rena Dye
*Assistant Examiner* — James Yager
(74) *Attorney, Agent, or Firm* — Young & Thompson

(57) ABSTRACT

A water-degradable sheet undergoes biodegradation and prevents drainage facilities (e.g., a sewage treatment tank) from clogging. The sheet includes a water-degradable substrate and a water-resistant layer, along with an enzyme that acts to decompose the substrate. The water-degradable sheet can reconcile water resistance with water solubility. The water-degradable sheet dissolves in water after immersion in water. The water-resistant layer can also contain a biodegradable substrate. An excretion receptacle having a pouch that includes the water-degradable sheet is also provided.

14 Claims, No Drawings

WATER-DISINTEGRABLE SHEET AND POUCH MADE OF THE SAME FOR EXCRETA-HOLDING WEAR

FIELD OF THE INVENTION

The present invention relates to a water-degradable sheet.

The invention also relates to a water-degradable sheet for use for disposing excrement, excretion fluid, gas, exudate, secretion fluid and the like from human bodies (hereinafter these are referred to as "excrement" as a generic term), and to a pouch for a body waste collector comprised of the same.

More precisely, the invention relates to a water-degradable sheet that permits a man a normal life with fitting it on for a period of time and after used, can be disposed of in a flush toilet with no trouble, and to a pouch for a body waste collector comprised of the same.

BACKGROUND OF THE INVENTION

Heretofore, in case where one could not control stool or urine excretion by own intention, or in case where one has a digestive system or urinary system disorder, the intestinal tract or urinary duct is led out to the body surface by surgical operation and a stoma is formed on the body surface. When a stoma is formed, in general, an ostomy pouch is fitted to the stoma for temporarily collecting excrement from the stoma.

In case where one has a body opening or wound in the body surface owing to any other disease, it is known to fit a drainage pouch to the opening or wound for disposing of excrement discharged by drainage or the like.

Many improvements have been made repeatedly on ostomy pouches and drainage pouches (hereinafter these may be simply referred to as "pouch for a body waste collector"), and essential problems in practical use are being solved in points of smell prevention and wearability improvement.

However, current pouches for a body waste collector still have serious problems on disposal of excrement.

Specifically, when excrement is collected in a pouch, the pouch must be disposed of after excrement therein is disposed of. For disposing of excrement, it must be drained off or must be scraped out. The operation is troublesome, and is an unpleasant operation owing to the bad smell of excrement and inevitable stool adhesion. In addition, the operation requires some space, and there may be a risk that the pouch may be damaged during the operation causing excrement to leak out of the pouch.

Accordingly, as a method for disposing of excrement collected in a pouch, there are disclosed a lot of techniques of flushing away the pouch for a body waste collector along with excrement therein in a flush toilet (for example, see Patent Reference 1).

Patent Reference 1: JP-T 2007-508905

However, for flushing away a pouch in a toilet, the pouch must have mechanical strengths to such a degree that it does not leak excrement for a period of time even while it keeps excrement collected therein (or that is, even while it is in wet), and on the other hand, when it is disposed of in a flush toilet, it must be disintegrated and decomposed so as not to clog up a septic tank and others. Accordingly, there is a problem that it is difficult to achieve both water resistance and water-degradability.

SUMMARY OF THE INVENTION

The invention has been made in consideration of the above-mentioned problems, and is to provide a water-degradable sheet that achieves both water resistance and water-degradability and a pouch comprised of the same for a body waste collector.

To solve the above-mentioned problems, the water-degradable sheet of the invention is a water-degradable sheet characterized in that it contains an enzyme.

The water-degradable sheet of the invention may comprise a water-degradable substrate and an enzyme that acts on the water-degradable substrate.

In the water-degradable sheet of the invention, the enzyme to decompose the water-degradable substrate may be contained in the water-degradable substrate.

In the water-degradable sheet of the invention, the water-degradable substrate may comprise an easily water-degradable layer and a water-resistant layer.

In the water-degradable sheet of the invention, the enzyme may be contained in the water-resistant layer.

In the water-degradable sheet of the invention, the water-resistant layer may comprise a biodegradable substrate.

In the water-degradable sheet of the invention, the enzyme may comprise at least one of a polysaccharide-degrading enzyme or a protease.

In the water-degradable sheet of the invention, the enzyme may form a concentration gradation in the water-resistant layer.

In the water-degradable sheet of the invention, the easily water-degradable layer may comprise water-degradable paper.

For solving the above-mentioned problems, the pouch for a body waste collector of the invention is a pouch for a body waste collector characterized in that it is comprised of a water-degradable sheet.

For solving the above-mentioned problems, the pouch for a body waste collector of the invention is a pouch for a body waste collector that comprises an inner pouch comprised of a water-degradable sheet and an outer pouch comprised of a non-water-degradable sheet to cover the outer side of the inner pouch.

The water-degradable sheet and the pouch comprised of the same for a body waste collector of the invention can degrade in water, and can be flushed away directly as such in a flush toilet, therefore facilitating excrement disposal.

In addition, they can be flushed away directly as such in a flush toilet, therefore facilitating the exchange operation even in narrow public toilets and others.

Further, in case where the pouch has a two-layered pouch structure comprising the water-degradable pouch of the invention and, covering the same, a non-water-degradable pouch, only the inner pouch may be disposed of and the outer pouch can be used repeatedly. Accordingly, it is economical as its costs can be reduced.

DETAILED DESCRIPTION OF THE INVENTION

The water-degradable sheet of the invention comprises an enzyme and a water-degradable substrate. In the invention, "water-degradable" is used to indicate the property that the sheet is disintegrated or decomposed when brought into contact with running water or a large amount of water, including a concept of a "water-soluble" property which permits the water-degradable sheet to dissolve in water to give a uniform solution.

Preferably, the thickness of the water-degradable sheet of the invention is from 20 to 250 µm, more preferably from 50 to 150 µm.

The water-degradable substrate is a sheet-like substance that is degraded with water when dipped in water.

The water-degradable substrate for use in the invention preferably comprises an easily water-degradable layer and a water-resistant layer formed on one side thereof.

The easily water-degradable layer in the invention comprises water-degradable paper and water-degradable resin film.

The water-degradable paper is a type of paper of such that, when stirred in warm water or cold water, the constitutive fibers dissolve or disperse therein. "Paper" as referred to herein is paper in a broad sense of the word, including paper and nonwoven fabric.

The water-degradable paper includes, for example, one produced through alkali treatment of unprocessed paper that contains fibrous carboxymethyl cellulose (JP-B 42-2925, etc.); one produced by infiltrating a water-soluble binder into fibers without bonding them through mechanical felting (JP-B 39-152, etc.); one produced by adhering an alkali metal compound to unprocessed paper that contains water-insoluble but alkali-soluble fibrous carboxymethyl cellulose salt (JP-B 43-28766, etc.); one produced by controlling the beating degree as in unprocessed toilet paper (Japanese Patent 3472494, etc.); air-laid nonwoven fabric constituted of pulp, cotton and others (JP-A 2006-565, etc.); etc.

Preferably, the thickness of the water-degradable paper is from 5 µm to 150 µm, more preferably from 10 µm to 80 µm.

The water-degradable paper may be suitably selected depending on the necessary softness and strength, the easiness in forming the water-resistant layer, etc.

In case where water-degradable paper is used for the water-degradable substrate, a pouch sheet for a body waste collector can be obtained, which has good softness in such a degree that it does not give any unpleasant feel to users and has mechanical strength to such a degree that it can keep the collected excrement for a predetermined period of time, and which, when disposed of in a flush toilet, can well dissolve or disperse in water.

On the other hand, the water-degradable resin film is a resin film composed of a resin that dissolves or disperses when the film is stirred in warm water or cold water.

For the water-degradable resin, a hydrophilic polymer compound can be used, and its examples include a polyvinyl alcohol film having a controlled degree of saponification, a methyl/ethyl cellulose film, etc.

The method for forming the water-degradable resin film is not specifically defined. For example, a resin may be shaped into a sheet according to an inflation method, a T-die method, a calendering method, an extrusion method, etc.

Preferably, the thickness of the water-degradable resin film is from 3 µm to 1.50 µm, more preferably from 10 µm to 80 µm.

Even when a water-degradable resin film is used for the water-degradable substrate, a pouch sheet for a body waste collector can be obtained, which has good softness and has good mechanical strength and water solubility or water dispersibility, as is in the case water-degradable paper is used.

The water-resistant layer in the invention comprises one that is more hardly disintegrable/decomposable than the easily water-degradable layer.

Preferably, the water-resistant layer comprises a biodegradable substrate.

The biodegradable substrate is preferably one having suitable mechanical strength during use, and capable of disintegrating and decomposing in water when the water-degradable sheet is disposed of in a flush toilet after use.

As the biodegradable substrate, concretely usable is a biodegradable polymer such as polysaccharide, protein, lipid, biodegradable resin, etc.; and especially preferred is polysaccharide or protein.

The polysaccharide includes, for example, starch, cellulose, and their modified products and derivatives, etc. Of those, preferred is starch; and more preferred are modified starch and dry starch.

Preferably, the particle size of the polysaccharide is from 5 µm to 100 µm, more preferably from 5 µm to 20 µm.

The protein includes collagen, gelatin, collagen peptide, and their modified products and derivatives, etc. Of those, preferred are gelatin and collagen peptide; and more preferred is collagen peptide.

If desired, chitin, chitosan, pectin and the like may also be used.

One or more biodegradable substrates may be used either singly or as combined.

The proportion of the biodegradable substrate in the water-resistant layer is preferably from 15% by weight to 80% by weight, more preferably from 25% by weight to 45% by weight.

The water-resistant layer may comprise a biodegradable resin, which is a type of synthetic biodegradable polymer. Addition of a biodegradable resin to the layer may increase the mechanical strength of the layer. The proportion of the biodegradable resin in the water-resistant layer is preferably from 15% by weight to 45% by weight, more preferably from 20% by weight to 35% by weight.

Not specifically defined, the biodegradable resin concretely includes polycaprolactone, polylactic acid-based resin, polybutylene succinate, polybutylene succinate adipate, etc.

Preferably, the thickness of the water-resistant layer is from 5 µm to 150 µm, more preferably from 40 µm to 90 µm.

Regarding the method of forming the water-resistant layer on the water-degradable paper or the water-degradable resin film constituting the easily water-degradable layer, the layer may be formed by coating, lamination or the like, though not specifically defined thereto.

Enzyme for use in the invention is preferably one that acts on the water-degradable substrate.

"Action by enzyme" as referred to herein means that the enzyme hydrolyzes or modifies the water-degradable substrate to thereby make the water-degradable substrate easily disintegrate and decompose.

The enzyme to be contained in the water-degradable sheet of the invention is preferably one having the activity of decomposing the biodegradable substrate under an anaerobic condition such as in a septic tank or the like and under a low water temperature condition, and more preferably one capable of specifically responding to the biodegradable substrate in the water-resistant layer.

Preferably, the enzyme is suitably selected in accordance with the biodegradable substrate; and when two or more biodegradable substrates are in the layer, enzymes corresponding to the individual biodegradable substrates are used, preferably, as combined.

In case where the biodegradable substrate is starch, the enzyme is preferably amylase, concretely including α-amylase, β-amylase and glucoamylase. Of those, preferred is α-amylase.

In case where the biodegradable substrate is collagen peptide, the enzyme is preferably protease, and its concrete examples include serine proteinase, aspartic proteinase, metal proteinase and thiol proteinase. Of those, preferred is serine proteinase.

In case where the biodegradable substrate is a mixture of starch and collagen peptide, the enzymes are preferably α-amylase and serine proteinase, as mixed, corresponding to starch and collagen peptide, respectively.

In the invention, the enzymes are not limited to natural enzymes and, for example, also adoptable are non-proteinaceous substitute molecules such as coenzymes, and artificial enzymes capable of specifically acting in accordance with the environmental situation, etc. Especially for the artificial enzymes, preferred are those capable of sufficiently decomposing the biodegradable substrate owing to the enzymatic activity thereof even though the water temperature is low.

In the invention, the enzyme must be contained in the water-degradable substrate.

The enzyme may adhere to the surface of the water-degradable sheet, or may be in the easily water-degradable layer; but preferably, it is contained in the water-resistant layer, more preferably in the biodegradable substrate in the water-resistant layer.

The method for incorporating the enzyme into the water-degradable sheet is not specifically defined and concrete example thereof includes a carrier bonding method (physical adsorption method, ion bonding method, covalent bonding method or biochemical specific bonding method), a crosslinking method, a clathration method (lattice clathration or microcapsule clathration), or their combination.

In the invention, preferred is a physical adsorption method, a clathration method or their combination.

The amount of the enzyme to be used is preferably from 0.05% by weight to 5% by weight relative to the total weight of the water-degradable sheet, more preferably from 0.1% by weight to 2% by weight.

In the invention, in case where the enzyme exists in the water-resistant layer, preferably, the enzyme distribution in the water-resistant layer is graded to thereby make an enzyme concentration gradation, or also preferably, the biodegradable substrate distribution is graded. In this case, preferably, the enzyme amount on the side nearer to the easily water-degradable layer is made larger and the enzyme amount on the side remoter from the easily water-degradable layer is made smaller. Accordingly, the water-degradable sheet may have more excellent durability during use and may have more excellent disintegrability and decomposability in water after use.

The method for forming the concentration gradation is not specifically defined. For example, in forming the water-resistant layer by coating, adoptable is a method of sequentially applying coating liquids having a different concentration, or a method of forming a multilayer structure by laminating a plurality of water-resistant layers having a different concentration.

Additive may be incorporated into the water-degradable sheet of the invention. Additive may impart softness, toughness and durability to the water-degradable sheet. The additive for use in the invention is preferably one capable of uniformly dispersing the biodegradable substrate and the enzyme in the biodegradable resin.

The additive usable in the invention includes one having a plasticizing effect, for example, phthalate plasticizer, trimellitate plasticizer, fatty acid plasticizer, epoxy plasticizer, adipate plasticizer, polyester plasticizer, fatty acid amide lubricant, fatty acid alcohol lubricant, montan wax, etc. More preferred are polyester plasticizer and montan wax.

The polyester plasticizer includes adipates, benzyl-2-(2-methoxyethoxy)ethyl adipate, poly(1,3-butanediol adipate).

The montan wax includes montanic acid wax, partially saponified montanic ester wax, and montanic ester wax.

The additive usable in the invention includes anionic surfactants, cationic surfactants, nonionic surfactants, ampholytic surfactants, higher alcohols, polyhydric alcohols and fatty acids.

The polyhydric alcohol includes glycerin, aliphatic polybasic acid esters, aliphatic polyhydric alcohol esters, oxyacid esters, rosin derivatives, etc.

The amount of the additive to be used is preferably from 5% by weight to 60% by weight relative to the water-degradable sheet, more preferably from 30% by weight to 50% by weight.

Further, a filler, a pH controlling agent and any other controlling agent may be suitably incorporated in the water-degradable sheet of the invention, so far as they do not detract from the object of the invention.

The pouch for a body waste collector of the invention is comprised of the water-degradable sheet of the invention. Concretely, the water-degradable sheet of the invention is heat-sealed at its peripheral edges with the water-resistant layer thereof kept facing each other to construct a pouch, which is further worked to have an opening hole corresponding to a stoma and is designed to fit to a face plate.

The structure of the pouch for a body waste collector is not specifically defined, and may be any known one. For example, a coupling member may be provided so as to fit to a face plate, and the coupling member may be removed from the pouch when the pouch is disposed of in a toilet.

The pouch may be so designed that it is put to the joint part between the outer bag and the face plate without a coupling member provided thereto. Further, the pouch may be stuck to a face plate so as to be removable along with the outer bag.

Preferably, the pouch for a body waste collector of the invention comprises an inner pouch comprised of a water-degradable sheet and an outer pouch comprised of a non-water-degradable sheet to cover the outside of the inner pouch.

The pouch for a body waste collector has an opening hole corresponding to a stoma and is so designed to fit to a face plate, and this is used as a two-layered structure comprised of an outer bag (outer pouch) of a non-water-degradable pouch of a plastic film or the like for deodorization and safety, and an inner bag (inner pouch) of the water-degradable pouch to be put inside it.

This constitution permits removal of only the inner pouch while the outer pouch can be repeatedly used and therefore is economical. In addition, as the frequency of putting on/off of a body waste collector to be fitted to the skin with an adhesive may be reduced, and even the person who has weak skin can well use the pouch with reduced irritation to the skin.

Further, when excrement is fluid owing to some physical condition, and even when the water-degradable sheet is thereby disintegrated, the outer pouch may protect excrement from leaking out.

The pouch for a body waste collector of the invention preferably has the following characteristics.

In the invention, even when an enzyme is in the water-resistant layer, the enzyme does not exert influences on the water-resistant layer. This may be considered because, since water does not exist in the water-resistant layer, the enzyme could not freely move inside the water-resistant layer.

However, when the water-degradable sheet is dipped in water, water penetrates into the water-resistant layer via the easily water-degradable layer. Accordingly, it may be considered that the enzyme can randomly move inside the water-resistant layer and, as a result, the enzyme decomposes the biodegradable substrate.

It is considered that the water-resistant layer is not decomposed by water in excrement. This is because the aqueous ingredient of excrement contains not only water but also various body substances, and therefore it is unsuitable for enzyme movement in the water-resistant layer.

False stools were sealed in the pouch for a body waste collector, and kept hung in an atmosphere at a temperature of 34° C. and a humidity of 97% for 8 hours, and in that condition, the liquid ingredient of the false stools put in the pouch does not bleed out.

The above-mentioned temperature and humidity may be considered nearly the same as the condition in which the pouch for a body waste collector is fitted to a body. The bleeding includes not only a case where the bleeding amount is great and the liquid ingredient begins to drip off from the pouch surface but also a case where the water-soluble paper is slightly wetted at a part of the pouch surface.

In addition, when the pouch for a body waste collector of the invention is, after kept hung under the above-mentioned condition, disposed of in the running water in a flush toilet, its easily water-degradable layer dissolves and its water-resistant layer is brought into contact with water in the toilet. Afterwards, it flows down in the drainage route and with the lapse of time, and it is gradually disintegrated and decomposed.

For facilitating disintegration thereof in the running water in a flush toilet, the pouch for a body waste collector may have some brittle parts such as grooves provided in any desired site thereof.

EXAMPLES

The invention is described in more detail with reference to the following Examples, to which, however, the invention should not be limited. In the Examples, part and % are by weight, unless otherwise specifically indicated.

The method for producing test pouches and the methods for evaluating the properties of the water-degradable sheet in the Examples are mentioned below.

(Test Pouches)

A water-degradable sheet having a length of 170 mm and a width of 110 mm is heat-sealed at three sides thereof with its water-resistant layer kept facing inside, thereby producing a test pouch.

(False Stools)

False stools comprising an aqueous 8 wt. % solution of potato starch (trade name "Katakuri-ko" by IY Foods) are used in tests The amount used is 130 g.

(Durability Test)

130 g of false stools are put into the test pouch, the upper opening is closed, and the pouch is kept hung in an atmosphere at a temperature of 34° C. and a humidity of 97% for 8 hours. The pouch is checked for water imperviousness through the sheet surface, for the breakage of the seal part and for cracks owing to the breakage of the pouch, and the pouch is evaluated according to the following standards:
  A: Four samples all had none of surface bleeding, explosion and breakage at the heat-sealed part.
  B: No sample exploded, but at least one sample had surface bleeding.
  C: At least one sample exploded.

(Breakage in Toilet)

This test is applied to the samples that passed the standard in the durability test.

A western-style, tank-connected flush toilet (TOTO's trade name "C770") is used. A test pouch is sunk in the toilet bowl filled with water, after 1 minute, this is flushed down through a drainage pipe, then collected at a length of 1.5 m of the pipe, and is checked for the condition thereof. The pouch is evaluated according to the following standards:
  A: All the samples fractured, came to pieces and lost their original shape.
  B: The samples did not explode to have waved cracks throughout the entire surface thereof, but the heat-sealed edges tore.
  C: The samples did not degrade at all. Specifically, at least one sample did not explode to have waved cracks throughout the entire surface thereof and its heat-sealed edges had no cracks.

(Degradation Test)

A test pouch is kept dipped in water at 10° C. for 3 hours, and before and after dipping, the weight change (weight reduction) of the pouch is determined. The pouch dipped in water is, after water is wiped away from it, spontaneously dried in an environment at 23° C. and a humidity of 65% for at least 24 hours, and then its weight is measured.

The weight reduction is determined according to the following formula:

Weight Reduction(%)=[((weight of pouch before dipping)−(weight of pouch after dipping))/(weight of pouch before dipping)]×100    [Numerical Formula 1]

Example 1

16.7% by weight of potato-derived starch (particle size, 5 to 100 μm) (Nippon Starch Chemicals trade name "ST Starch P"), 16.7% by weight of fish-derived collagen peptide (Nitta Gelatin's trade name "Ixos HDL-50SP"), 1.2% by weight of glycerin (NOF's trade name "Conc-Glycerin") and 13.3% by weight of adipate (Kao's trade name "HA-5") were mixed at room temperature (hereinafter this is referred to as "mixture 1").

26.7% by weight of polycaprolactone (Daicel Chemical Industry's trade name "Placcel H7"), 6.7% by weight of poly(1,3-butanediol adipate) (Daihachi Chemical Industry's trade name "BAA-15") and 16.7% by weight of adipate were kept at 140° C. for 3 hours, and then kneaded at 140° C. for 10 minutes (hereinafter this is referred to as "mixture 2").

The mixture 1 and the mixture 2 were mixed, kneaded at 120° C. for 10 minutes, then controlled down to 70° C., and 1.0% by weight of α-amylase (Nagase ChemteX's trade name "Spitase XP-404") and 1.0% by weight of protease (Nagase ChemteX's trade name "Bioplase AL-15FG") were added thereto, and kneaded at 70° C. for 3 minutes (this is hereinafter referred to as "mixture 3").

Through a rolling machine under a condition of a temperature of 70° C., the mixture 3 was formed into a film having a thickness of 70 μm, and then laminated on one surface of a sheet of water-soluble paper having a unit weight of 30 g/m$^2$ and a thickness of 65 μm (Mishima Paper Manufacturing's trade name "MDP-30"; corresponding to "easily water-degradable layer") using a laminator under a condition of a temperature of 70° C., thereby producing a test pouch sheet.

Next, four test pouches were formed of it, then 130 g of false stools were put into each pouch, and finally the opened one side of each pouch was heat-sealed.

The test pouches were tested for the durability test and the explosion test in toilet. The results are shown in Table 1.

In the degradation test, the water-resistant layer alone not laminated with water-soluble paper was tested.

Example 2

Test pouches were produced and evaluated in the same manner as in Example 1, for which, however, the amount of potato-derived starch was changed to 8.3%, fish-derived collagen peptide was to 25.0% and glycerin was to 1.3% by weight. The results are shown in Table 1.

Example 3

Test pouches were produced and evaluated in the same manner as in Example 1, for which, however, the amount of potato-derived starch was changed to 25.0%, fish-derived collagen peptide was to 8.3% and glycerin was to 1.3% by weight The results are shown in Table 1.

Comparative Example 1

Test pouches were produced and evaluated in the same manner as in Example 1, for which however enzyme was not used. The results are shown in Table 1.

Example 4

17.7% by weight of modified esterified starch (particle size, 5 to 20 m) (Nippon StarchChemical's trade name "Octie"), 8.9% by weight of fish-derived collagen peptide (Nitta Gelatin's trade name "Ixos HDL-50SP"), 4.0% by weight of glycerin and 8.0% by weight of montanate wax (Clariant Japan's trade name "Licolub WE40") were mixed at room temperature (hereinafter this is referred to as "mixture 4").

24.2% by weight of polycaprolactone (Daicel Chemical Industry's trade name "Placcel H7"), 24.2% by weight of benzyl-2-(2-methoxyethoxy)ethyl adipate (Daihachi Chemical Industry's trade name "DAIFATTY®-101") and 12.1% by weight of acetylated monoglyceride (Riken Vitamin's trade name "Rikemal PL-019") were kept at 140° C. for 3 hours, and then kneaded at 140° C. for 10 minutes (hereinafter this is referred to as "mixture 5").

The mixture 4 and the mixture 5 were mixed, kneaded at 120° C. for 10 minutes, then cooled down to 70° C., and 0.6% by weight of α-amylase (Nagase ChemteX's trade name "Spitase XP-404") and 0.3% by weight of protease (Nagase ChemteX's trade name "Bioplase AL-15FG") were added thereto, and kneaded at 70° C. for 3 minutes (this is hereinafter referred to as "mixture 6").

Through a laminator and a rolling machine under a condition of a temperature of 70° C., the mixture 6 was formed into a film having a thickness of 85 μm on one surface of a sheet of water-soluble paper having a unit weight of 30 g/m² and a thickness of 65 μm (Mishima Paper Manufacturing's trade name "MDP-30"; corresponding to "easily water-degradable layer"), as laminated on the water-soluble paper, thereby producing a sheet of test pouch.

Next, four test pouches were formed of it, then 130 g of false stools were put into each pouch, and finally the opened one side of each pouch was heat-sealed.

The test pouches were tested for the durability test and the explosion test in toilet. The results are shown in Table 1.

In the degradation test, the water-resistant layer alone not laminated with water-soluble paper was tested.

Example 5

Test pouches were produced and evaluated in the same manner as in Example 4, for which, however, the amount of each ingredient to be used was changed as in Table 1. The results are shown in Table 1.

Example 6

Test pouches were produced and evaluated in the same manner as in Example 4, for which, however, the amount of each ingredient to be used was changed as in Table 1. The results are shown in Table 1.

Comparative Example 2

Test pouches were produced and evaluated in the same manner as in Example 6, for which however enzyme was not used. The results are shown in Table 1.

TABLE 1

| | | Example 1 | Example 2 | Example 3 | Comparative Example 1 |
|---|---|---|---|---|---|
| Mixture 1 | | | | | |
| Polysaccharide | Unmodified starch (*2) | 16.7% | 8.3% | 25.0% | 17.7% |
| Protein | Fish-derived collagen peptide (*3) | 16.7% | 25.0% | 8.3% | 17.7% |
| Additive | Glycerin (*4) | 1.2% | 1.3% | 1.3% | 1.2% |
| Additive | Adipate (*6) | 13.3% | 13.3% | 13.3% | 13.3% |
| Mixture 2 | | | | | |
| Biodegradable resin | Polycaprolactone (*10) | 26.7% | 26.7% | 26.7% | 26.7% |
| Additive | Aliphatic polyester (*7) | 6.7% | 6.7% | 6.7% | 6.7% |
| Additive | Adipate (*6) | 16.7% | 16.7% | 16.7% | 16.7% |
| Enzyme | | | | | |
| α-Amylase (*11) | | 1.0% | 1.0% | 1.0% | — |
| Protease (*12) | | 1.0% | 1.0% | 1.0% | — |
| Total Amount | | 100.0% | 100.0% | 100.0% | 100.0% |
| Durability Test | | A | A | A | A |
| Explosion Test in toilet | | A | A | A | A |
| Degradation Test (weight reduction) | | 31.6% | 24.9% | 33.7% | 8.6% |

TABLE 1-continued

|  |  | Example 4 | Example 5 | Example 6 | Comparative Example 2 |
|---|---|---|---|---|---|
| Mixture 4 | | | | | |
| Polysaccharide | Esterified starch (*1) | 17.7% | 15.6% | 22.2% | 17.9% |
| Protein | Fish-derived collagen peptide (*3) | 8.9% | 15.6% | 11.1% | 8.9% |
| Additive | Glycerin (*4) | 4.0% | 7.1% | 5.0% | 4.1% |
| Additive | Montanic composite ester wax (*5) | 8.0% | 7.1% | 10.0% | 8.1% |
| Mixture 5 | | | | | |
| Biodegradable resin | Polycaprolactone (*10) | 24.2% | 21.3% | 20.2% | 24.4% |
| Additive | Acetylated monoglyceride (*8) | 12.1% | 10.8% | 10.1% | 12.2% |
| Additive | BEA (*9) | 24.2% | 21.3% | 20.2% | 24.4% |
| Enzyme | | | | | |
| α-Amylase (*11) | | 0.6% | 0.6% | 0.8% | — |
| Protease (*12) | | 0.3% | 0.6% | 0.4% | — |
| Total Amount | | 100.0% | 100.0% | 100.0% | 100.0% |
| Durability Test | | A | A | A | A |
| Explosion Test in toilet | | A | A | A | A |
| Degradation Test (weight reduction) | | 33.9% | 34.7% | 32.3% | 8.7% |

(Footnotes to Table 1)
(*1): Octie
(*2): ST Starch P
(*3): HDL-50SP
(*4): Glycerin
(*5): Licolub WE40
(*6): HA-5
(*7): BAA-15
(*8): PL-019
(*9): DAIFATTY-101 (benzyl-2-(2-methoxyethoxy)ethyl adipate
(*10): PCL Placcel H7
(*11): Spitase XP-404
(*12): Bioplase AL-15FG As shown in Table 1, the samples of Examples 1 to 6 had good results in the durability test and in the explosion test in toilet. These samples also had good results in the degradation test in that the weight reduction thereof was approximately from 3 to 4 times that of the samples of Comparative Example 1 and Comparative Example 2.

This confirms that the mechanical strength of these samples to keep excrement collected in the pouches is good and, when disposed of in toilets, these samples exhibits good water solubility or water dispersibility.

In particular, in Examples 1, and 3 to 6, the weight reduction in the degradation test was at least 30%, and this confirms that the enzyme efficiently decomposes the biodegradable substrate in these samples.

The reason why the weight reduction in Example 1 and Example 3 was high would be because the starch decomposition was more efficient than the collagen peptide decomposition. The weight reduction in Examples 4 to 6 was also high, and the reason would be because the amount of glycerin was increased to thereby increase the hydrophilicity of the film, and water could more readily penetrate into the inside of the film. As a result, the enzyme could be more active in these samples.

In Examples 1 to 6, the preferred range of amylase is from 0.3 to 1.51% by weight. When it is less than 0.3% by weight, then the enzyme could not sufficiently decompose the substrate; however, when more than 1.51% by weight, the weight reduction may increase in accordance with the increase in the amount of the enzyme, but the decomposability itself could not be enhanced. On the other hand, the amount of the protease is preferably within a range of from 0.08 to 0.61% by weight. When it is less than 0.08% by weight, collagen could not be sufficiently decomposed; but even when it is more than 0.61% by weight, the weight reduction could no more change.

In Examples 4 to 6, the amount of benzyl-2-(2-methoxyethoxy)ethyl adipate is preferably within a range of from 16.4 to 28.2% by weight. When it is less than 16.4% by weight, the melt viscosity could not lower, and the biodegradable substrate and the enzyme could not be uniformly dispersed in polycaprolactone; but when more than 28.2% by weight, the additive may bleed out.

As in Table 1, the weight reduction of the test pouches is preferably at least 15%, more preferably at least 20%, even more preferably at least 30%.

On the other hand, the quality of the water-degradable sheets of Comparative Example 1 and Comparative Example 2 was on the same level as that in Examples 1 to 6 in point of the durability and the explosion in toilet; but in the degradation test, the weight reduction of the comparative samples was only on a level of slight dissolution of starch or collagen in water. This is because the comparative water-degradable sheets did not contain an enzyme.

The water-degradable sheets of the invention are applicable to any other use than that for pouches for a body waste collector.

For example, the water-degradable sheet of the invention can be used as an adhesion-preventive membrane. With this, adhesion of organs to each other in surgical operations can be prevented. In addition, since the water-degradable sheet can be decomposed in bodies, it is free from a trouble of taking out the adhesion-preventive membrane in re-operation, and the load to the patient body can be relieved and the operation costs and others can be reduced.

The water-degradable sheet of the invention is also usable for disposable bags or for simple toilets in disasters, etc. Using it may simplify the disposal of excrements and others.

Further, the water-degradable sheet of the invention is usable for excrement collectors for use in walking with pets. Using this, pet owners may dispose of pet's excrements along with the water-degradable sheet.

Further, the water-degradable sheet of the invention may be used as paper mats or disposal sheets for pus basins, bedpans, etc.

The invention claimed is:

1. A water-degradable sheet, comprising:
a water-degradable substrate; and
an enzyme that acts to decompose the water-degradable substrate,
wherein,
the water-degradable substrate comprises an easily water-degradable layer and a water-resistant layer that is less easily water-degradable than the water-degradable layer, and
the water-resistant layer comprises a biodegradable resin comprising one or more polymer selected from the group consisting of: polycaprolactone, polylactic acid-based resin, polybutylene succinate and polybutylene succinate adipate.

2. The water-degradable sheet as claimed in claim 1, wherein the enzyme is contained in the water-degradable substrate.

3. The water-degradable sheet as claimed in claim 1, wherein the enzyme is contained in the water-resistant layer.

4. The water-degradable sheet as claimed in claim 1, wherein the enzyme comprises at least one of a polysaccharide-degrading enzyme or a protease.

5. The water-degradable sheet as claimed in claim 3, wherein the enzyme forms a concentration gradation in the water-resistant layer.

6. The water-degradable sheet as claimed in claim 1, wherein the easily water-degradable layer comprises water-degradable paper or water-degradable resin film.

7. A pouch for an excretion receptacle comprised of a water-degradable sheet of claim 1.

8. A pouch for an excretion receptacle, comprising:
an inner pouch comprised of a water-degradable sheet; and
an outer pouch comprised of a non-water-degradable sheet and covering an outer side of the inner pouch,
wherein the inner pouch is comprised of the water-degradable sheet of claim 1.

9. The water-degradable sheet as claimed in claim 2, wherein the enzyme comprises at least one of a polysaccharide-degrading enzyme or a protease.

10. The water-degradable sheet as claimed in claim 3, wherein the enzyme comprises at least one of a polysaccharide-degrading enzyme or a protease.

11. The disposable sheet according to claim 1, wherein the sheet comprises 0.1-2 wt % of enzyme, relative to total weight of the sheet.

12. A disposable sheet, comprising:
(i) a water-degradable layer comprising water-degradable paper, water-degradable resin or a mixture thereof; and
(ii) a biodegradable layer comprising (a) a mixture of polysaccharide, protein, and biodegradable resin, and (b) amylase and protease enzymes that is are active on the biodegradable layer, said biodegradable layer formed on one side of the water-degradable layer,
wherein the biodegradable layer is more water-resistant than the water-degradable layer.

13. The disposable sheet according to claim 12, wherein the biodegradable layer comprises:
(a) starch, collagen peptide, and polycaprolactone; and
(b) α-amylase and protease.

14. The disposable sheet according to claim 12, wherein the biodegradable layer is a single layer.

* * * * *